United States Patent
Sartipi et al.

(10) Patent No.: US 12,202,794 B2
(45) Date of Patent: Jan. 21, 2025

(54) METHODS FOR ISOMERIZING ALPHA OLEFINS

(71) Applicants: Sina Sartipi, Willebroek (BE); Wenyih Frank Lai, Bridgewater, NJ (US); Roxana Perez Velez, Leuven (BE); Renyuan Yu, Humble, TX (US); Paul F. Keusenkothen, Houston, TX (US); Zsigmond Varga, Schaerbeek (BE)

(72) Inventors: Sina Sartipi, Willebroek (BE); Wenyih Frank Lai, Bridgewater, NJ (US); Roxana Perez Velez, Leuven (BE); Renyuan Yu, Humble, TX (US); Paul F. Keusenkothen, Houston, TX (US); Zsigmond Varga, Schaerbeek (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 3 days.

(21) Appl. No.: 17/907,131

(22) PCT Filed: Mar. 22, 2021

(86) PCT No.: PCT/EP2021/057185
§ 371 (c)(1),
(2) Date: Sep. 23, 2022

(87) PCT Pub. No.: WO2021/191105
PCT Pub. Date: Sep. 30, 2021

(65) Prior Publication Data
US 2023/0109131 A1    Apr. 6, 2023

Related U.S. Application Data

(60) Provisional application No. 62/993,173, filed on Mar. 23, 2020.

(30) Foreign Application Priority Data

Jun. 4, 2020 (EP) .................................... 20178316

(51) Int. Cl.
C07C 5/27 (2006.01)
B01J 29/65 (2006.01)
C07C 11/02 (2006.01)

(52) U.S. Cl.
CPC ............. *C07C 5/2737* (2013.01); *B01J 29/65* (2013.01); *C07C 11/02* (2013.01); *C07C 2529/65* (2013.01)

(58) Field of Classification Search
CPC ......... C07C 5/27; C07C 5/2737; C07C 11/02; C07C 2529/65; B01J 29/65
See application file for complete search history.

(56) References Cited

U.S. PATENT DOCUMENTS 4,375,573 A    3/1983  Young
6,054,415 A *  4/2000  Gee ........................ C10G 45/64
                                                            585/666

FOREIGN PATENT DOCUMENTS

EP      2043774 B1    6/2011
WO      94/25417 A1   11/1994
(Continued)

OTHER PUBLICATIONS

Extended European Search Report received for European Patent Application No. 20178316.4 mailed on Nov. 20, 2020, 5 Pages.
(Continued)

*Primary Examiner* — In Suk C Bullock
*Assistant Examiner* — Jason Y Chong

(57) ABSTRACT

A method for isomerizing alpha olefins to produce an isomerization mixture comprising branched olefins can comprise contacting an olefinic feed including one or more $C_{10}$-$C_{20}$ alpha olefins with a catalyst under skeletal isomer-
(Continued)

ization conditions, wherein the catalyst comprises a molecular sieve having an MRE topology; and obtaining an isomerization mixture comprising one or more $C_{10}$-$C_{20}$ branched olefins.

16 Claims, 3 Drawing Sheets

(56) References Cited

FOREIGN PATENT DOCUMENTS

| WO | 2018/166689 A1 | 9/2018 | |
|---|---|---|---|
| WO | WO-2019118230 A1 * | 6/2019 | ............. B01J 29/06 |
| WO | 2021/191105 A1 | 9/2021 | |

OTHER PUBLICATIONS

International Preliminary Report on Patentability received for PCT Application No. PCT/EP2021/057185, mailed on Oct. 6, 2022, 7 Pages.

International Search Report and Written Opinion received for PCT Application No. PCT/EP2021/057185, mailed on May 17, 2021, 12 Pages.

* cited by examiner

METHODS FOR ISOMERIZING ALPHA OLEFINS

This application is a National Phase Application claiming priority to PCT Application Serial No. PCT/EP2021/057185 filed Mar. 22, 2021, which claims priority to and the benefit of U.S. Provisional Application No. 62/993,173 filed Mar. 23, 2020 and European Patent Application No. 20178316.4 filed Jun. 4, 2020.

FIELD OF THE INVENTION

This application relates to methods for isomerizing alpha olefins to produce an isomerization mixture comprising branched olefins.

BACKGROUND

Branched olefins are commercially valuable for use in a variety of applications such as intermediates in the manufacture of industrial fluids, cleaning agents, and solvent products. For example, branched olefins may be hydrotreated to provide fluids exhibiting a number of desirable properties, such as biodegradability and low viscosity and/or hydroformylated to provide alcohol products.

Branched olefins may be produced via the skeletal isomerization of alpha olefins. In the skeletal isomerization of alpha olefins to branched olefins suitable for subsequent hydrogenation or hydroformylation via Oxo processes (see, e.g., EP2043774 B1), it is desirable to produce an isomerization mixture having a combination of a reduced pour point while maintaining acceptable biodegradability. The pour point of the isomerization mixture generally decreases with increasing conversion of alpha olefins to internal olefins and with increasing formation of branched olefins. In contrast, the biodegradability of the isomerization mixture generally increases with decreased formation of branched olefins, particularly those having extended branching.

Accordingly, there is a need for highly active and selective methods of isomerizing alpha olefins to branched olefins at high conversion and with a controlled amount of linear olefin formation.

SUMMARY

This application relates to methods for isomerizing alpha olefins to produce an isomerization mixture comprising branched olefins.

Methods described herein may comprise contacting an olefinic feed comprising one or more $C_{10}$-$C_{20}$ alpha olefins with a catalyst under skeletal isomerization conditions, wherein the catalyst comprises a molecular sieve having an MRE topology; and obtaining an isomerization mixture comprising one or more $C_{10}$-$C_{20}$ branched olefins.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this application.

DETAILED DESCRIPTION

Figure 1:
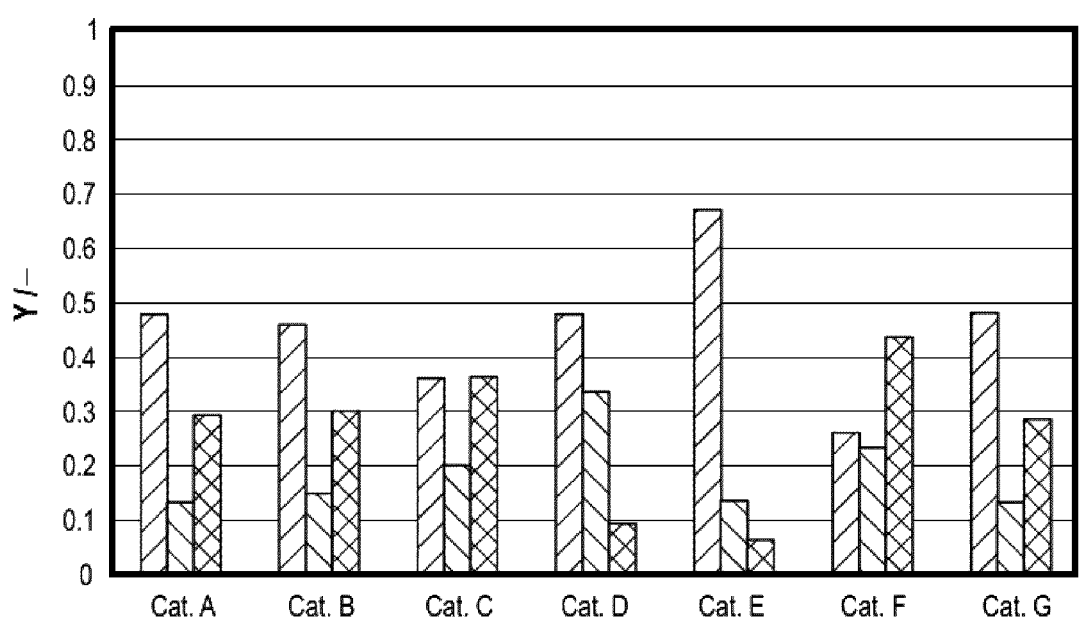
FIG. 1 depicts a bar graph showing the reaction yields of the isomerization reactions of $C_{14}$ alpha olefins using various catalysts producing linear internal olefins (left histograms), $C_{14}$ branched olefins (middle histograms), and $C_{20+}$ olefins (right histograms) of Example 1.

This application relates to methods for isomerizing alpha olefins to produce an isomerization mixture comprising branched olefins.

These methods require an olefinic feed including one or more $C_{10}$-$C_{20}$ alpha olefins and a catalyst to provide mixtures having $C_{10}$-$C_{20}$ branched olefins.

The methods described herein may use catalysts including molecular sieves having an MRE topology.

All numerical values within the detailed description and the claims herein are modified by "about" or "approximately" the indicated value, and take into account experimental error and variations that would be expected by a person having ordinary skill in the art. Unless otherwise indicated, room temperature is about 23° C.

Definitions

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first mixture are expressed based on the total weight of the first mixture. All ranges expressed herein should include both end points as two specific embodiments unless specified or indicated to the contrary.

The term "hydrocarbon" means a class of compounds containing hydrogen bound to carbon, and encompasses (i) saturated hydrocarbon compounds; (ii) unsaturated hydrocarbon compounds; and (iii) mixtures of hydrocarbon compounds (saturated and/or unsaturated), including mixtures of hydrocarbon compounds having different values of n, i.e. differing carbon numbers.

As used herein, a "carbon number" refers to the number of carbon atoms in a hydrocarbon. Likewise, a "$C_x$" hydrocarbon is one having x carbon atoms (i.e., carbon number of x), and a "$C_x$-$C_y$" or "$C_{x-y}$" hydrocarbon is one having from x to y carbon atoms.

The term "alkane" refers to non-aromatic saturated hydrocarbons with the general formula $C_nH_{(2n+2)}$, where n is 1 or greater. An alkane may be straight chained or branched. Examples of alkanes include, but are not limited to methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

The term "olefin," alternatively referred to as "alkene," refers to a branched or unbranched unsaturated hydrocarbon having one or more carbon-carbon double bonds. A simple olefin comprises the general formula $C_nH_{2n}$, where n is 2 or greater. Examples of olefins include, but are not limited to ethylene, propylene, butylene, pentene, hexene and heptene. "Olefin" is intended to embrace all structural isomeric forms of an olefin. For example, butylene encompasses but-1-ene, (Z)-but-2-ene, etc.

As used herein, the term "molecular sieve" is used synonymously with the term "zeolite" or "microporous crystalline material."

As used herein, the term "reactor" refers to any vessel(s) in which a chemical reaction occurs. Reactor includes both distinct reactors, as well as reaction zones within a single reactor apparatus and, as applicable, reaction zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

Various embodiments described herein provide processes for the production of one or more $C_{10}$-$C_{20}$ branched olefins via isomerization, typically catalytic isomerization, of one or more $C_{10}$-$C_{20}$ alpha olefins. It has been found that employing molecular sieve catalysts having an MRE topology in the isomerization advantageously allows for the isomerization to be conducted under mild process conditions, particularly at low temperature. Conducting the isomerization at a low temperature provides several benefits, such as reducing energy usage of the process and improving selectivity to desired products in the resulting isomerization mixture. Additionally, it has been found that such catalysts are particularly effective in controlling branched olefin formation in the produced isomerization mixture. Generally, the resulting isomerization mixture comprises a minimized linear olefin content in a range low enough to maintain biodegradability properties of the mixture while high enough to maintain an acceptably low pour point. For example, the isomerization of the $C_{10}$-$C_{20}$ alpha olefinic feed using a catalyst having a molecular sieve having an MRE framework topology results in a conversion of the $C_{10}$-$C_{20}$ alpha olefins in a range from about 20% to about 98%, such as from about 20% to about 95%, or from about 40% to about 90%, from about 50% to about 85%, or from about 60% to about 80%.

Olefinic Feed

Generally, the alpha olefins supplied to the isomerization have a carbon number ranging from 10 to 20, more preferably from 12 to 18, more preferably from 12 to 16, and ideally from 12 to 14. Preferably, the alpha olefins supplied to the isomerization are linear alpha olefins.

Typically, the one or more $C_{10}$-$C_{20}$ alpha olefins are provided in an olefinic feed. Suitable olefinic feeds for use in various embodiments of the present invention comprise (or consist essentially of, or consist of) $C_{10}$-$C_{20}$ alpha olefins, preferably $C_{12}$-$C_{18}$ alpha olefins, such as $C_{12}$-$C_{16}$ alpha olefins, ideally $C_{12}$-$C_{14}$ alpha olefins. In any embodiment, at least about 50 wt %, preferably at least about 60 wt %, more preferably at least about 80 wt %, more preferably at least about 85 wt %, more preferably at least about 95 wt %, more preferably at least about 99 wt % of the olefinic feed is composed of alpha olefins, preferably alpha olefins, having any of the aforementioned $C_x$-$C_y$ ranges (i.e., any of the aforementioned numbers of carbon atoms) based on the total weight of the olefinic feed. For example, in any embodiment the olefinic feed may comprise from about 40 wt % to 100 wt %, such as from about 75 wt % to about 90 wt %, of alpha olefins, preferably linear alpha olefins, having any of the aforementioned $C_x$-$C_y$ ranges based on the total weight of the olefinic feed. Particularly preferable olefinic feeds may comprise $C_{12}$-$C_{16}$ alpha olefins, ideally $C_{12}$-$C_{14}$ linear alpha olefin mixtures. In such aspects, the olefinic feed typically comprises at least about 40 wt % of $C_{14}$ alpha olefins, more preferably at least about 60 wt %, such as at least about 65 wt % of $C_{14}$ alpha olefins (preferably linear $C_{14}$ alpha olefins) based on the total weight of the olefinic feed and, additionally or alternatively, at most about 60 wt %, more preferably at most about 40 wt %, such as at most about 35 wt % of $C_{14}$ alpha olefins (preferably linear $C_{14}$ alpha olefins) based on the total weight of the olefinic feed, such as from about 60 wt % or from about 65 wt % to 75 wt % $C_{14}$ alpha olefins and from about 25 wt % to about 40 wt % or to about 35 wt % $C_{14}$ alpha olefins based on the total weight of the olefinic feed.

In any embodiment, the olefinic feed preferably has an average carbon number (by weight, as measured by GC-MS) of greater than or equal to 12, preferably less than or equal to 16, such as from 12 to 16.

Typically, the olefinic feed is substantially linear. For example, the olefinic feed typically has a branched olefin content of less than 10 wt % based on the total weight of the olefinic feed, preferably less than about 8 wt %, more preferably less than about 4 wt %, such as from 0 wt % to 10 wt % branched olefin content based on the total weight of the olefinic feed.

Preferably, the olefinic feed is pretreated prior to isomerization to remove moisture, oxygenates, nitrates, and other impurities that could deactivate the isomerization catalyst. Typically, the pretreatment is performed by passing the feed through a guard bed that contains a sieve. Typically, the pretreated feed comprises less than about 50 ppmw water based on the weight of the feed, more preferably less than about 25 ppmw.

Skeletal Isomerization Catalyst

Generally, the isomerization is conducted in the presence of a catalyst. Typically, the isomerization catalyst comprises (or consists essentially of, or consists of) a molecular sieve of the MRE family. Preferably, the molecular sieve is of the ZSM-48 family. The term "ZSM-48 family material" (or "material of the ZSM-48 family" or "molecular sieve of the ZSM-48 family"), as used herein, includes one or more of:

molecular sieves made from a common first degree crystalline building block unit cell, which unit cell has the MRE framework topology (A unit cell is a spatial arrangement of atoms which if tiled in three-dimensional space describes the crystal structure. Such crystal structures are discussed in the "Atlas of Zeolite Framework Types," Fifth edition, 2001, the entire content of which is incorporated as reference);

molecular sieves made from a common second degree building block, being a 2-dimensional tiling of such MRE framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MRE framework topology. More particularly, ZSM-48 includes a family of materials having tubular pores. The pores are formed of rolled up honeycomb-like sheets of fused T6-rings (T=tetrahedral), and the pore aperture contains 10 T-atoms. Neighboring pores are related by a zero shift along the pore direction or by a shift of half the repeat distance along the pore direction.

Molecular sieves of ZSM-48 family generally have an X-ray diffraction pattern including d-spacing maxima at 11.8±0.2, 10.2±0.2, 7.2±0.15, 4.2±0.08, 3.9±0.08, 3.6±0.06, 3.1±0.05 and 2.85±0.05 Angstrom. The X-ray diffraction data used to characterize the material are obtained by standard techniques using the K-alpha doublet of copper as the incident radiation and a diffractometer equipped with a scintillation counter and associated computer as the collection system.

Molecular sieves of ZSM-48 (ZSM-48 and the conventional preparation thereof are taught by U.S. Pat. No. 4,375, 573) may include pure ZSM-48 crystals. Substantially pure ZSM-48 crystals are defined herein as ZSM-48 crystals that contain less than 20 wt % of another type of zeolite and/or impurity, such as ZSM-50 or Kenyaite. Preferably, the substantially pure ZSM-48 crystals can contain less than 15 wt % of another type of zeolite, such as less than 10 wt % of another type of zeolite, or less than 5 wt % of another type of zeolite. More preferably, the substantially pure ZSM-48 crystals can contain less than 20 wt % of another type of zeolite (such as ZSM-50) or an impurity such as Kenyaite. In such aspects, the substantially pure ZSM-48 crystals can contain less than 15 wt % of another type of zeolite or impurity, such as less than 10 wt % of another type of zeolite or impurity, or less than 5 wt % of another type of zeolite or impurity, and mixtures thereof. The molecular sieves of ZSM-48 family may also include post-synthesis crystallites such as steamed versions.

Additionally, the molecular sieve of the ZSM-48 family (MRE topology) has a $Si/Al_2$ molar ratio of less than or equal to 200, or of about 50 to about 200, or of about 60 to about 175, or of about 65 to about 150, or of about 70 to about 125, or of about 80 to about 100, or of about 85 to about 95.

The isomerization catalyst may be composited with a porous matrix binder material such as clay and/or inorganic oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable inorganic oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form to facilitate extrusion of the catalyst composition. Typically, the binder material may be present from about 0 wt % to about 90 wt % based on the weight of the isomerization catalyst, such as from about 20 wt % to about 50 wt %.

Alternately, the isomerization catalyst may be substantially free of binder, or free of binder. Typically, the isomerization catalyst is free or substantially free of additional components apart from the molecular, binder (if present), and optionally, trace amounts of alkali and/or alkali earth metals or compounds thereof. For example, in any embodiment the isomerization catalyst may be free or substantially free from promoters, such as noble metals and transition metals in metal or metal oxide form, e.g., platinum, palladium, ruthenium, iron, cobalt, and nickel. For instance, preferably the isomerization catalyst may comprise a combined platinum, palladium, ruthenium, iron, cobalt, and nickel content of less than about 0.5 wt % based on the weight of the isomerization catalyst, more preferably less than about 0.1 wt % or less than about 0.01 wt %.

Isomerization of Olefins

The isomerization reaction can be conducted in a wide range of reactor configurations including fixed bed (single or in series) and fluidized bed, preferably fixed bed. In addition, the isomerization can be conducted in a single reaction zone or in a plurality of reaction zones.

Typically, the isomerization is conducted under conditions suitable to maintain the reaction medium in the liquid phase. Preferably, the isomerization is conducted under mild process conditions, particularly at low temperature. Suitable reaction temperatures range from at least about 100° C., such as from about 100° C. about 300° C., such as from about 100° C. to about 200° C., such as from about 120° C. to about 190° C., or from about 140° C. to about 180° C., or from about 150° C. to about 170° C., while suitable isomerization pressures range from about 0.5 barg to about 2 barg, or more preferably from about 1 barg to about 2 barg. Preferably, the olefinic feed is supplied to the reaction at a weight hourly space velocity (WHSV) ranging from about 1 $h^{-1}$ to about 50 $h^{-1}$, more preferably from about 1 $h^{-1}$ to about 20 $h^{-1}$, more preferably from about 1 $h^{-1}$ to about 10 $h^{-1}$, wherein the WHSV is the weight of feed flowing per unit weight of the catalyst per hour. The temperature ranges may also vary with the activity loss of the catalyst, e.g., the temperature range may be increased to compensate for catalyst activity losses.

Typically, the isomerization exhibits a high single-pass rate of conversion (measured as 100 minus the remaining amount of linear alpha olefins expressed in wt %, as measured by GC). For example, preferably the single-pass rate of conversion of the one or more $C_{10}$-$C_{20}$ alpha olefins is from about 5% to about 98%, more preferably from about 20% to about 98%. In such aspects, the isomerization can be conveniently conducted in the absence of recycle, i.e., without recycling any portion of the produced isomerization mixture. Preferably, conducting the isomerization without recycle provides several process advantages, such as increasing process reliability and reducing operating costs.

Preferably, the isomerization reaction is highly selective to the desired branched olefin products, and exhibits minimal side reactions, such as oligomerization and cracking. For example, typically less than about 30 wt % of $C_{10}$-$C_{20}$ alpha olefins present in the olefinic feed are converted to product having a lower or higher carbon number. Additionally or alternatively, typically less than about 30 wt % of linear $C_{10}$-$C_{20}$ alpha olefins present (if any) in the olefinic feed are converted to $C_{20+}$ olefins.

Isomerization Mixture

The resulting isomerization mixture obtained via isomerization of the one or more $C_{10}$-$C_{20}$ alpha olefins according to any one or more of the foregoing embodiments typically comprises (or consists essentially of, or consists of) linear internal olefins, branched olefins, e.g., branched internal olefins, and, optionally, $C_{20+}$ olefins. For example, the isomerization mixture preferably has a branched olefin content of from about 5 wt % to about 98 wt %, preferably from about 10 wt % to about 95 wt %, such as from about 20 wt % to about 90 wt %, or from about 25 wt % to about 85 wt % based on the total weight of the isomerization mixture. The isomerization mixture may further comprise from 0 wt % to about 90 wt %, preferably from about 10 wt % to about 85 wt %, more preferably from about 15 wt % to about 80 wt % of linear internal olefins based on the total weight of the isomerization mixture. The isomerization mixture may further comprise less than about 20 wt % of $C_{20+}$ olefins or dimerized olefins, such as less than about 15 wt %, or less than about 10 wt %, or less than about 7 wt % of $C_{20+}$ olefins or dimerized olefins.

The isomerization product may also contain some amount of residual $C_{10}$-$C_{20}$ alpha olefins. Preferably, the isomerization mixture comprises a residual $C_{10}$-$C_{20}$ alpha olefin content of less than about 35 wt %. In a first alternative, the isomerization mixture contains less than about 10 wt %, and ideally less than about 5 wt %, such as less than about 3 wt % of residual $C_{10}$-$C_{20}$ alpha olefins based on the total weight of the isomerization mixture. In a second alternative, the isomerization mixture contains from about 10 wt % to about 29 wt %, preferably from about 10 wt % to about 20 wt %, and ideally from about 10 wt % to about 15 wt %, of residual $C_{10}$-$C_{20}$ alpha olefins based on the total weight of the isomerization mixture.

In the present methods, it is found that molecular sieves having an MRE topology are particularly active for the skeletal isomerization of $C_{10}$-$C_{20}$ linear alpha olefins. In addition, such catalysts exhibit improved selectivity towards branched internal olefins while also providing improved control of $C_{20+}$ olefin formation.

For example, in a first alternative, using a molecular sieve having an MRE topology in the isomerization of a $C_{14}$ linear alpha olefin feed, it is found that the resulting isomerization mixture may comprise:

from about 5 wt % to about 98 wt % of branched olefins, such as from 10 wt % to about 95 wt %, such as from about 15 wt % to about 90 wt %, or from about 20 wt % to about 85 wt %;

from 0 wt % to about 90 wt %, such as 10 wt % to about 85 wt %, for example from about 15 wt % to about 80 wt % of linear internal olefins;

less than about 20 wt % of $C_{20+}$ olefins, such as $C_{28+}$ olefins, such as less than about 15 wt %, or less than about 10 wt %, or less than about 7 wt % of $C_{20+}$ olefins, such as $C_{28+}$ olefins; and less than about 10 wt %, such as less than about 5 wt %, for example less than about 3 wt % of linear alpha olefins.

Accordingly, in a first alternative, olefinic mixtures produced in accordance with the processes of the present disclosure may advantageously comprise from about 5 wt % to about 98 wt % of branched olefins, such as from 10 wt % to about 95 wt %, such as from about 15 wt % to about 90 wt %, or from about 20 wt % to about 85 wt % branched olefins; from 0 wt % to about 90 wt %, such as 10 wt % to about 85 wt %, for example from about 15 wt % to about 80 wt % of linear internal olefins; less than about 20 wt % of $C_{20+}$ olefins, such as $C_{28+}$ olefins, such as less than about 15 wt %, or less than about 10 wt %, or less than about 7 wt % of $C_{20+}$ olefins, such as $C_{28+}$ olefins; and less than about 10 wt %, such as less than about 5 wt %, for example less than about 3 wt % of linear alpha olefins.

In the second alternative, using a molecular sieve having an MRE topology in the isomerization of $C_{12}$ linear alpha olefin feed, it is found that the resulting isomerization mixture may comprise:

from about 5 wt % to about 98 wt % of branched olefins, such as from 10 wt % to about 95 wt %, such as from about 15 wt % to about 90 wt %, or from about 20 wt % to about 85 wt %;

from 0 wt % to about 90 wt %, such as 10 wt % to about 85 wt %, for example from about 15 wt % to about 80 wt % of linear internal olefins;

less than about 20 wt % of $C_{20+}$ olefins, such as $C_{24+}$ olefins such as less than about 15 wt %, or less than about 10 wt %, or less than about 7 wt % of $C_{24+}$ olefins; and less than about 10 wt %, such as less than about 5 wt %, for example less than about 3 wt % of linear alpha olefins.

Accordingly, in a second alternative, olefinic mixtures produced in accordance with the methods of the present disclosure may advantageously comprise from about 5 wt % to about 98 wt % of branched olefins, such as from 10 wt % to about 95 wt %, such as from about 15 wt % to about 90 wt %, or from about 20 wt % to about 85 wt % branched olefins; from 0 wt % to about 90 wt %, such as 10 wt % to about 85 wt %, for example from about 15 wt % to about 80 wt % of linear internal olefins; less than about 20 wt % of $C_{20+}$ olefins, such as $C_{24+}$ olefins, such as less than about 15 wt %, or less than about 10 wt %, or less than about 7 wt % of $C_{20+}$ olefins, such as $C_{24+}$ olefins; and less than about 10 wt %, such as less than about 5 wt %, for example less than about 3 wt % of linear alpha olefins.

In any embodiment, the branched olefins obtained in the isomerization mixture may be particularly useful as intermediates for hydrogenation for fluid applications and/or hydroformylation via the Oxo process for alcohol production. Preferred isomerization mixtures suitable for these applications may comprise 20 wt % or more of $C_{12}$-$C_{16}$ branched olefins. In an especially preferred embodiment, the isomerization mixture comprises, in a first alternative, about 20 wt % or more, in particular from about 5 wt % to about 98 wt % of $C_{12}$-$C_{16}$ branched olefins, such as from 10 wt % to about 95 wt %, such as from about 15 wt % to about 90 wt %, or from about 20 wt % to about 85 wt % $C_{12}$-$C_{16}$ branched olefins; from 0 wt % to about 90 wt %, such as 10 wt % to about 85 wt %, for example from about 15 wt % to about 80 wt % of $C_{12}$-$C_{16}$ linear internal olefins; less than about 20 wt % of $C_{20+}$ olefins, such as less than about 15 wt %, or less than about 10 wt %, or less than about 7 wt % of $C_{20+}$ olefins; and less than about 10 wt %, such as less than about 5 wt % of $C_{12}$-$C_{16}$ linear alpha olefins.

Example Embodiments

Embodiments disclosed herein include Embodiment A.

Embodiment A: A method comprising contacting an olefinic feed comprising one or more $C_{10}$-$C_{20}$ alpha olefins with a catalyst under skeletal isomerization conditions, wherein the catalyst comprises a molecular sieve having an MRE topology; and obtaining an isomerization mixture comprising one or more $C_{10}$-$C_{20}$ branched olefins.

Embodiment A may have one or more of the following additional elements in any combination:

Element 1: wherein the olefinic feed comprises one or more $C_{12}$-$C_{14}$ alpha olefins.

Element 2: wherein the molecular sieve is of the ZSM-48 family.

Element 3: wherein the catalyst is free of noble metals and transition metals in metal or oxide form.

Element 4: wherein the molecular sieve has a Si/Al$_2$ molar ratio of less than or equal to 200.

Element 5: wherein the molecular sieve has a Si/Al$_2$ molar ratio within a range of from about 50 to about 200.

Element 6: wherein the catalyst further comprises a binder selected from clay, inorganic oxides, and mixtures or combinations thereof.

Element 7: wherein the binder comprises silica and/or alumina.

Element 8: wherein the olefinic feed has an average carbon number of greater than or equal to 12.

Element 9: wherein the olefinic feed comprises $C_{14}$ alpha olefins at a concentration of at least about 40 wt % based on the total weight of the olefinic feed.

Element 10: wherein the olefinic feed comprises $C_{12}$ alpha olefins at a concentration of at least about 40 wt % based on the total weight of the olefinic feed.

Element 11: wherein the isomerization conditions comprise a temperature from at least about 100° C.

Element 12: wherein the olefin feed is supplied at a weight hourly space velocity (WHSV) from about 1 h$^{-1}$ to about 20 h$^{-1}$ based on liquid reactive feed and zeolite content of the catalyst.

Element 13: wherein the conversion of the $C_{10}$-$C_{20}$ alpha olefins is from about 20% to about 98%.

Element 14: wherein the conversion of the $C_{10}$-$C_{20}$ alpha olefins is from about 30% to about 98%.

Element 15: wherein the conversion of the $C_{10}$-$C_{20}$ alpha olefins is from about 60% to about 98%.

Element 16: wherein the isomerization mixture comprises $C_{10}$-$C_{20}$ branched olefins at a concentration from about 5 wt % to about 98 wt % based on the total weight of the isomerization mixture.

Element 17: wherein the isomerization mixture comprises $C_{10}$-$C_{20}$ branched olefins at a concentration from about 20 wt % to about 98 wt % based on the total weight of the isomerization mixture.

Element 18: wherein the isomerization conditions comprise a temperature from at least about 100° C., and wherein the isomerization mixture comprises $C_{10}$-$C_{20}$ linear internal olefins at a concentration from 0 wt % to about 90 wt % based on the total weight of the isomerization mixture.

Element 19: wherein the isomerization mixture comprises one or more $C_{20+}$ olefins at a concentration of about 30 wt % or less based on the total weight of the isomerization mixture.

Element 20: wherein the isomerization conditions comprise a temperature from about 100° C. to about 200° C., and wherein the one or more $C_{20+}$ olefins are at a concentration of about 1 wt % or less based on the total weight of the isomerization mixture.

Element 21: composition comprising the isomerization mixture produced by the method of Embodiment A.

Embodiment A may have one or more of the following additional elements in any combination: Elements 1-19 and 21. In addition, by way of non-limiting example, exemplary combinations applicable to Embodiment A include: combinations of Elements 1 and 2; combinations of Elements 1-3; combinations of Elements 1-4; combinations of Elements 1-5; combinations of Elements 1-6; combinations of Elements 1-7; combinations of Elements 1-8; combinations of Elements 1-9; combinations of Elements 1-10; combinations of Elements 1-11; combinations of Elements 1-12; combinations of Elements 1-13; combinations of Elements 1-14; combinations of Elements 1-15; combinations of Elements 1-16; combinations of Elements 1-17; combinations of Elements 1-18; combinations of Elements 1-19; combinations of Elements 1-19 and 21; combinations of Elements 2 and 3; combinations of Elements 2, 3, and 4; combinations of Elements 19 and 20; combinations of Elements 19, 20, and 21; combinations of Element 1 with one or more of Elements 2-19 with Element 21; combinations of Element 2 with one or more of Elements 3-19 with Element 21; combination of Element 3 with one or more of Elements 4-19 with Element 21; combination of Element 4 with one or more of Elements 5-19 with Element 21; combination of Element 5 with one or more of Elements 6-19 with Element 21; combination of Element 6 with one or more of Elements 7-19 with Element 21; combination of Element 7 with one or more of Elements 8-19 with Element 21; combination of Element 8 with one or more of Elements 9-19 with Element 21; combination of Elements 19 and 20.

To facilitate a better understanding of the embodiments described herein, the following examples of various representative embodiments are given. In no way should the following examples be read to limit, or to define, the scope of the present disclosure.

EXAMPLES

Example 1

A series of catalysts based on MCM-22 (Catalyst A), MCM-49 (Catalysts B and C), ZSM-48 with a Si/Al$_2$ ratio of 70 (Catalyst D), ZSM-11 (Catalyst E), MCM-41 (Catalyst F), and ZrO$_x$-doped alumina (Catalyst G) were used in isomerization reactions of $C_{14}$ linear alpha olefins. Table 1 shows the structural and textural details and chemical properties of these catalysts. The catalysts were not steamed.

TABLE 1

|  | Cat A | Cat B | Cat C | Cat D | Cat E | Cat F | Cat G |
| --- | --- | --- | --- | --- | --- | --- | --- |
| Zeolite | MCM-22 | MCM-49 | MCM-49 | ZSM-48 | ZSM-11 | N/A$^a$ | N/A |
| Si/Al2 of zeolite | 23 | 17-18 | 17-18 | 70 | 50 | N/A | N/A |
| Binder | V-300 | V-300 | Al$_2$O$_3$ | V-300 | V-300 | V-300 | N/A |
| Topology | MWW | MWW | MWW | MRE | MEL | N/A | N/A |
| Ring | 10 | 10 | 10 | 10 | 10 × 8 | N/A | N/A |
| Dimensionality | 2 | 2 | 2 | 1 | 3 | N/A | N/A |

TABLE 1-continued

| | Cat A | Cat B | Cat C | Cat D | Cat E | Cat F | Cat G |
|---|---|---|---|---|---|---|---|
| $S_{BET}$ (m$^2$ g$^{-1}$) | N/D[b] | 536 | 579 | 301 | 426 | 779 | 449 |
| $S_{ext}$ (m$^2$ g$^{-1}$) | N/D | 184 | 104 | 231 | 224 | 256 | 468 |
| $V_{micro}$ (cm$^3$ g$^{-1}$) | N/D | 0.14 | 0.19 | 0.03 | 0.09 | 0.36 | 0 |
| α | N/D | 520 | N/D | 65 | 410 | N/D | 37.1 |
| ncollidine (μmol g$^{-1}$) | N/D | 76 | 122 | 69 | N/D | 269.4 | 205.7 |

[a]Not applicable
[b]Not determined

The isomerization reactions of a $C_{14}$ linear alpha olefin feed containing >99.5 wt % $C_{14}$ with ca. 95 wt % linear alpha olefins and ca. 0.2 wt % paraffins using Catalysts A-G were performed at 140-180° C. and 0-1.5 barg with WHSVs set at 1-10 h$^{-1}$, based on liquid reactive feed and active phase content of the catalysts. Occasionally trans-decalin (Merck, 821745) was added into the feed as internal standard in order to determine the mass-balance. Once a reasonable mass-balance was assured, no internal standard was used. The reaction yields were collected after 64 h on-stream. Three reactions were identified, namely, a double-bond shift converting the $C_{14}$ linear alpha olefins into linear internal olefins, a skeletal isomerization converting the $C_{14}$ linear alpha olefins into branched hydrocarbons, and into $C_{20+}$ olefins. The reactions yields for the three different products resulting from the isomerization reactions of the $C_{14}$ linear alpha olefins using Catalysts A-G are shown in FIG. 1. The ZSM-48-based catalyst (Catalyst D) provided the highest yield of $C_{14}$ branched olefins while maintaining the dimerization activity at low levels, as compared with other materials based on MCM-22 (Catalyst A), MCM-49 (Catalysts B and C), MCM-41 (Catalyst F), and ZrO$_x$-doped alumina (Catalyst G).

Examples 2-7

Isomerization reactions of $C_{14}$ linear alpha olefins were conducted using a catalyst based on ZSM-48 Si/Al$_2$=90 (Catalyst H). Table 2 shows the structural and textural details and chemical properties of Catalyst H. Catalyst H was not steamed.

TABLE 2

| | Cat H |
|---|---|
| Zeolite | ZSM-48 |
| Si/Al2 of zeolite | 90 |
| Binder | V-300 |
| Topology | MRE |
| Ring | 10 |
| Dimensionality | 1 |
| $S_{BET}$ (m$^2$ g$^{-1}$) | 297 |
| $S_{ext}$ (m$^2$ g$^{-1}$) | 193 |
| $V_{micro}$ (cm$^3$ g$^{-1}$) | 0.05 |
| α | 54 |
| ncollidine (μmol g$^{-1}$) | N/D |

Figure 2:
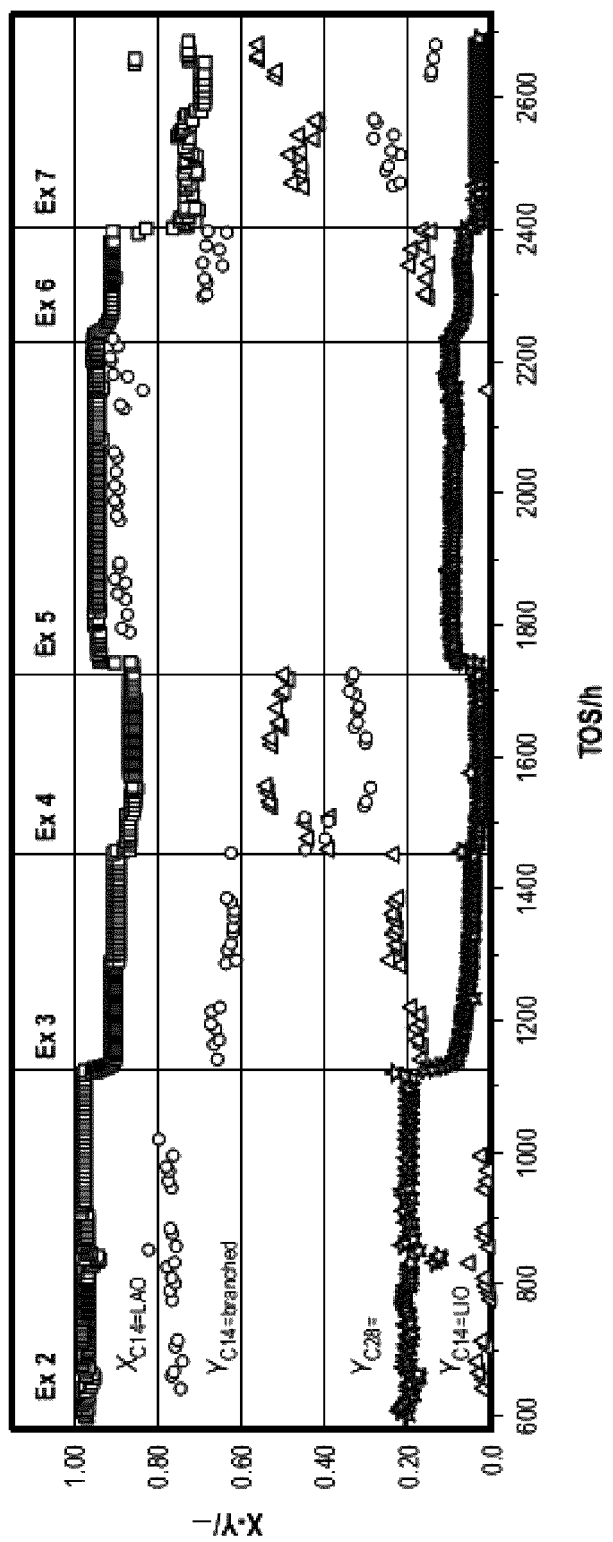
FIG. 2 depicts the linear internal olefin, branched olefin, and $C_{20+}$ olefin concentrations of the isomerization mixture against time on stream (TOS) produced in the isomerization reactions conducted in Examples 2-7.

FIG. 2 illustrates the on-stream stability of the ZSM-48-based catalyst with Si/Al$_2$ ratio of 90. Table 3 shows the various temperatures and space velocities employed through Examples 2-7. The pressure was 1.5 barg.

TABLE 3

| | Temperature (° C.) | WHSV[c] (h$^{-1}$) |
|---|---|---|
| Example 2 | 180 | 1 |
| Example 3 | 180 | 5 |

TABLE 3-continued

| | Temperature (° C.) | WHSV[c] (h$^{-1}$) |
|---|---|---|
| Example 4 | 170 | 5 |
| Example 5 | 170 | 1 |
| Example 6 | 160 | 1 |
| Example 7 | 160 | 5 |

[c]Reported WHSVs were set points, based on liquid reactive feed and zeolite content of the catalyst.

The conversion of linear alpha olefins (squares) to linear internal olefins (triangles), branched olefins (circles), and $C_{20+}$ olefins (stars) in the produced isomerization mixture against time on stream for Examples 2-7 are depicted in FIG. 2. As shown in FIG. 2, the dimerization is more pronounced at higher temperatures and longer residence times. However, the highest yield to dimers is at ca. 20% even at such severe conditions (FIG. 2—Ex 2).

The yield of $C_{14}$ branched olefins is higher than that of $C_{14}$ linear internal olefins at higher temperatures and shorter residence times (FIG. 2—Ex 2, 3, 5, and 6). The highest yield of $C_{14}$ branched olefins is obtained at ca. 90% at 170° C. with a WHSV of 1 h$^{-1}$ (FIG. 2—Ex 4). This yield is very close to the total $C_{14}$ linear alpha olefins conversion at corresponding process conditions. Such high yields of branched olefins are necessary to achieve pour points smaller than −30° C., after hydrogenation of the hydrocarbon for fluids applications.

Examples 8-10

Figure 3:
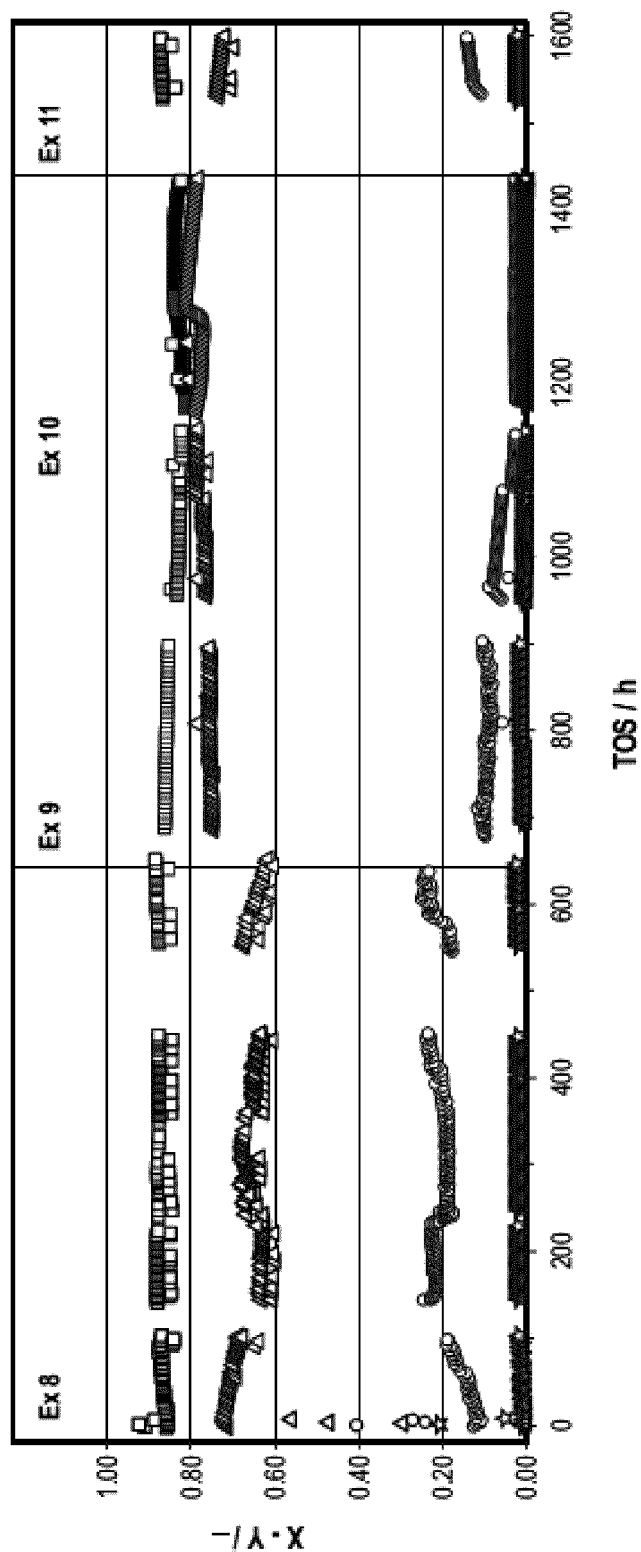
FIG. 3 depicts the linear internal olefin, branched olefin, and $C_{20+}$ olefin concentrations of the isomerization mixture against time on stream (TOS) produced in the isomerization reactions conducted in Examples 8-11.

Isomerization reactions of $C_{14}$ linear alpha olefins were conducted using Catalyst D. FIG. 3 illustrates the on-stream stability of the ZSM-48-based catalyst with Si/Al$_2$ ratio of 70. Table 4 shows the various temperatures and space velocities employed through Examples 8-10. The pressure was 1.5 barg.

TABLE 4

| | Temperature (° C.) | WHSV[d] (h$^{-1}$) |
|---|---|---|
| Example 8 | 150 | 5 |
| Example 9 | 150 | 10 |
| Example 10 | 140 | 10 |
| Example 11 | 150 | 5 |

[d]Reported WHSVs were set points, based on liquid reactive feed and zeolite content of the catalyst.

The conversion of $C_{14}$ alpha olefins (circles) to linear internal olefins (triangles), branched olefins (circles), and dimers (stars) in the produced isomerization mixture against time on stream for Examples 8-11 are depicted in FIG. 3. As illustrated in FIG. 3, at lower temperatures the $C_{20+}$ olefins formation drops to almost zero after a few hours of reaction over the ZSM-48-based catalyst in Examples 8-11 (FIG. 3—Exs 8-11). The highest yield to $C_{14}$ linear internal olefins is obtained at ca. 80% at 140° C. with WHSV of 10 h$^{-1}$ (FIG. 3—Ex 10). This yield is almost equal to the total $C_{14}$ linear alpha-olefin conversion at corresponding process conditions. After 1400 h on-stream, process conditions were set back to initial values in FIG. 3. While $C_{14}$ linear alpha olefin conversion stays similar, the yield to branched olefins slightly decreases and that to $C_{14}$ linear internal olefins increases (FIG. 3, Ex 8 vs. Ex 11).

Hydroformylation of such linear internal olefins may increase the overall yield to mono methyl branched alcohols via Oxo process. A necessity for this Oxo process is that the hydroformylation catalyst should not have significant double-bond shift activity.

Examples 2-11, as illustrated in FIGS. 2 and 3, demonstrate that ZSM-48-based catalysts represent stable catalytic performance for over 2600 h on-stream (>4200 $kg_{feed}$ $kg^{-1}{}_{catalyst}$) at various process conditions.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby.

Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa. The term "and/or" as used in a phrase such as "A and/or B" herein is intended to include "A and B," "A or B," "A," and "B." Numerical ranges used herein include the numbers recited in the range. For example, the numerical range "from 1 wt % to 10 wt %" includes 1 wt % and 10 wt % within the recited range.

The invention claimed is:

1. A method comprising:
   contacting an olefinic feed consisting essentially of $C_{12}$-$C_{14}$ alpha olefins with a catalyst under skeletal isomerization conditions, wherein the catalyst comprises a molecular sieve having an MRE topology, wherein the olefinic feed has an average carbon number from 12 to 14 and is supplied at a weight hourly space velocity (WHSV) of about 1 h$^{-1}$ based on liquid reactive feed and zeolite content of the catalyst, and wherein the isomerization conditions comprise a temperature of about 170° C.; and
   obtaining an isomerization mixture consisting essentially of $C_{12}$-$C_{14}$ branched olefins.

2. The method of claim 1, wherein the molecular sieve is of the ZSM-48 family.

3. The method of claim 1, wherein the catalyst is free of noble metals and transition metals in metal or oxide form.

4. The method of claim 1, wherein the molecular sieve has a Si/Al$_2$ molar ratio of less than or equal to 200.

5. The method of claim 1, wherein the molecular sieve has a Si/Al$_2$ molar ratio within a range of from about 50 to about 200.

6. The method of claim 1, wherein the olefinic feed comprises $C_{14}$ alpha olefins at a concentration of at least about 40 wt % based on a total weight of the olefinic feed.

7. The method of claim 1, wherein the olefinic feed comprises $C_{12}$ alpha olefins at a concentration of at least about 40 wt % based on the total weight of the olefinic feed.

8. The method of claim 1, wherein a conversion of the $C_{12}$-$C_{14}$ alpha olefins is from about 20% to about 98%.

9. The method of claim 1, wherein the conversion of the $C_{12}$-$C_{14}$ alpha olefins is from about 30% to about 98%.

10. The method of claim 1, wherein the isomerization mixture consists essentially of $C_{12}$-$C_{14}$ branched olefins at a concentration from about 5 wt % to about 98 wt % based on the total weight of the isomerization mixture.

11. The method of claim 1, wherein the isomerization mixture consists essentially of $C_{12}$-$C_{14}$ branched olefins at a concentration from about 20 wt % to about 98 wt % based on the total weight of the isomerization mixture.

12. The method of claim 1, wherein the isomerization mixture consists essentially of $C_{12}$-$C_{14}$ linear internal olefins at a concentration from 0 wt % to about 90 wt % based on the total weight of the isomerization mixture.

13. The method of claim 1, wherein the olefinic feed comprises $C_{14}$ alpha olefins at a concentration of at least about 60 wt % based on the total weight of the olefinic feed.

14. The method of claim 1, wherein the olefinic feed comprises $C_{12}$ alpha olefins at a concentration of at least about 60 wt % based on the total weight of the olefinic feed.

15. A method comprising:
   contacting an olefinic feed consisting essentially of $C_{12}$-$C_{14}$ alpha olefins with a catalyst under skeletal isomerization conditions, wherein the catalyst comprises a molecular sieve having an MRE topology and comprises ZSM-48, wherein the olefinic feed is supplied at a weight hourly space velocity (WHSV) of about 1 h$^{-1}$ based on liquid reactive feed and zeolite content of the catalyst, wherein the olefinic feed has an average carbon number from 12 to 14, and wherein the isomerization conditions comprise a temperature of about 170° C.; and
   obtaining an isomerization mixture consisting essentially of $C_{12}$-$C_{14}$ branched olefins.

16. The method of claim 15, wherein the olefinic feed comprises $C_{14}$ alpha olefins or $C_{12}$ alpha olefins at a concentration of at least about 40 wt % based on a total weight of the olefinic feed.

* * * * *